United States Patent
Gatfield et al.

(12) 
(10) Patent No.: US 6,331,655 B1
(45) Date of Patent: Dec. 18, 2001

(54) PROCESS FOR THE PREPARATION OF AROMATIC CARBONYL COMPOUNDS FROM STYRENES

(75) Inventors: Ian-Lucas Gatfield; Jens-Michael Hilmer, both of Höxter (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 09/591,637

(22) Filed: Jun. 9, 2000

(30) Foreign Application Priority Data

Jun. 19, 1999 (DE) ............................................... 199 28 158

(51) Int. Cl.[7] .......................... C07C 45/00; C07C 63/64; C07C 53/134; C07C 309/00; C12P 7/24
(52) U.S. Cl. .......................... 568/435; 568/310; 568/311; 568/426; 435/147; 562/495; 562/496; 560/104; 560/105
(58) Field of Search .................................... 568/311, 310, 568/435; 435/147, 830, 18; 426/44, 52; 562/495, 496; 560/104, 105

(56) References Cited

U.S. PATENT DOCUMENTS

| | | | |
|---|---|---|---|
| 3,102,081 | * 8/1963 | Faucett et al. . | |
| 5,017,388 | 5/1991 | Rabenhorst et al. | 426/44 |
| 5,034,471 | * 7/1991 | Blackborow . | |
| 5,128,253 | * 7/1992 | Labuda et al. . | |
| 5,358,861 | 10/1994 | Markus et al. | 435/147 |
| 5,536,661 | 7/1996 | Boel et al. | 435/254.3 |
| 5,541,092 | * 7/1996 | Kirk et al. . | |
| 5,712,132 | 1/1998 | Mane et al. | 435/147 |
| 5,766,912 | 6/1998 | Boel et al. | 435/198 |
| 5,861,286 | 1/1999 | Mane et al. | 435/74 |
| 5,866,380 | 2/1999 | Lesage-Meessen et al. | 435/146 |
| 5,866,406 | * 2/1999 | Wagner et al. . | |
| 5,965,384 | 10/1999 | Boel et al. | 435/69.1 |

FOREIGN PATENT DOCUMENTS

| | | |
|---|---|---|
| 375102 | 6/1990 | (EP) . |
| 542348 | 5/1993 | (EP) . |
| 0 845 532 | 6/1998 | (EP) . |
| 857789 | 8/1998 | (EP) . |
| 88/02775 | 4/1988 | (WO) . |
| 94/01541 | 1/1994 | (WO) . |
| 96/22381 | 7/1996 | (WO) . |
| 98/51811 | 11/1998 | (WO) . |

OTHER PUBLICATIONS

Derwent abstract (Acc. No. 1989–260902) of JP 96019027. Simultaneous preparation of aldehyde and epoxy compounds.*
Streitweiser et al. (1976). Introduction to Organic Chemistry. pp. 648–651.*
Directive 88/388/EEC, p. 1–8, Foodstuffs, Jun. 22, 1988.
J. Chem. Soc., Chem. Commun., (month unavailable) 1990, Björkling et al, Lipase–mediated Formation of Peroxycarboxylic Acids used in Catalytic Epoxidation of Alkenes, pp. 1301–1303.
J. Chem. Soc. Perkin Trans 1, (month unavailable) 1995, Lemoult et al, pp. 89–91, Lipase–Catalysed Baeyer–Villiger Reactions.

* cited by examiner

*Primary Examiner*—Paul J. Killos
*Assistant Examiner*—Mahreen Chaudhry
(74) *Attorney, Agent, or Firm*—Joseph C. Gil; Noland J. Cheung

(57) ABSTRACT

The present invention relates to a novel process for the preparation of aromatic carbonyl compounds by oxidative cleavage of styrenes using lipases and hydrogen peroxide or hydrogen peroxide donors in the presence of carboxylic acids or carboxylic esters.

13 Claims, No Drawings

PROCESS FOR THE PREPARATION OF AROMATIC CARBONYL COMPOUNDS FROM STYRENES

FIELD OF THE INVENTION

The present invention relates to a novel process for the preparation of aromatic carbonyl compounds by oxidatively cleaving styrenes using lipases and hydrogen peroxide or hydrogen peroxide donors in the presence of carboxylic acids or carboxylic esters.

BACKGROUND OF THE INVENTION

To prepare aromatic carbonyl compounds which are intended to be used as flavorings or fragrances, it is possible to utilize the oxidative cleavage of styrenes. For the preparation of vanillin, the oxidative cleavage of eugenol or isoeugenol with $K_2Cr_2O_7/H_2SO_4$ has been described. In industry, vanillin is prepared predominantly by the alkaline hydrolysis of lignin (spent sulphite liquor from the paper industry) and oxidative cleavage of the resulting coniferyl alcohol (Römpp Lexikon Chemie, Version 1.5).

However, the aromatic carbonyl compounds prepared in this manner, such as, for example, vanillin, have the disadvantage that they are not permitted to be referred to as natural flavorings but only as nature-identical flavorings within the meaning of Directive 88/388/EEC on flavorings. Only compounds which have been prepared by physical processes (e.g., distillation or extraction) or biotechnological processes (enzymatically or microbially) can be referred to as natural flavorings.

To prepare natural benzaldehyde, for example, cassia oil is treated with hot steam.

EP-A 542,348 describes a process for the preparation of natural phenylaldehydes using the enzyme lipoxidase. If the substrates used are eugenol or isoeugenol, the reaction with the lipoxidase gives vanillin. Disadvantages of this process are the low conversions of from 0.3 to 15%.

DE-A 19,649,655 describes a process for the preparation of vanillin from ferulic acid in the presence of the enzyme ferulic acid deacylase. However, the enzyme can only be used for the preparation of vanillin starting from ferulic acid. Other starting materials are not suitable.

U.S. Pat. No. 5,128,253 describes the preparation of natural vanillin from ferulic acid or eugenol by biotransformation. Microorganisms used are *Aspergillus niger, Rhodotorula glutinis* and *Corynebacterium glutamicum*. The main disadvantage in this preparation is the long incubation time of, on average, from 7 to 10 days.

EP-A 405,197 describes the preparation of natural vanillin by oxidation of eugenol or isoeugenol using microorganisms of the genera Serratia, Klebsiella or Enterobacter. Within short reaction times, this method too, permits only relatively low yields.

SUMMARY OF THE INVENTION

The object of the present invention was then to provide a process for the preparation of aromatic carbonyl compounds which can be used as natural flavors or fragrances, which is easy to carry out and produces the desired products in good yields and in short reaction times.

We have now found a process for the preparation of aromatic carbonyl compounds, which is characterized in that styrenes are oxidatively cleaved in the presence of carboxylic acids or carboxylic esters by lipases and hydrogen peroxide or hydrogen peroxide donors.

DETAILED DESCRIPTION OF THE INVENTION

The advantages of the process according to the present invention are high yields, simple implementation and simple isolation of the desired product. In addition, it is possible to react a variety of starting materials with the same lipase to give a variety of products which can be used as natural flavorings. The process according to the present invention, thus, represents a universally applicable process for the preparation of aromatic carbonyl compounds from styrenes.

Lipases are usually used for esterification or transesterification. There are numerous descriptions of these applications. The use of lipases for the enzymatic epoxidation of alkenes (WO 91/043333) and for the preparation of peroxycarboxylic acids from carboxylic acids has also been described. In addition, the reaction of sulphides to sulphoxides (Björkling et al., J. Chem. Soc., Chem. Commun., 1990, 1301–1303) and the lipase-catalyzed Baeyer-Villiger oxidation (Lemoult et al., J. Chem. Soc. Perkin Trans. 1, 1995, 89–91) have been described.

In the process according to the present invention, in the first reaction step, the corresponding peroxycarboxylic acid forms from the carboxylic acid or the carboxylic ester and hydrogen peroxide. This acid reacts with the styrene used, producing, as reaction products, aromatic carbonyl compounds and the corresponding carboxylic acid.

The styrenes are preferably compounds of the formula (I)

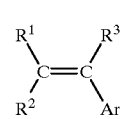

(I)

in which
$R^1$, $R^2$ and $R^3$ independently of one another are hydrogen, straight-chain or branched $C_1$–$C_{20}$-alkyl, $C_3$–$C_8$-cycloalkyl, $C_6$–$C_{14}$-aryl, $C_7$–$C_{15}$-arylalkyl, $C_1$–$C_{20}$-alkoxy, $C_1$–$C_{20}$-alkylamino, wherein the above-mentioned hydrocarbon radicals may be mono- or polysubstituted by hydroxyl, formyl, oxy, $C_1$–$C_6$-alkoxy, carboxyl, mercapto, sulpho, amino, $C_1$–$C_6$-alkylamino, nitro or halogen, and Ar is phenyl, optionally mono- or polysubstituted with straight-chain or branched $C_1$–$C_6$-alkyl, $C_3$–$C_8$-cycloalkyl, $C_1$–$C_6$-alkoxy, hydroxyl, oxy, carboxyl, mercapto, sulpho, amino, $C_1$–$C_6$-alkylamino, nitro or halogen.

In a preferred embodiment, styrenes of the formula (I) are used
in which
$R^1$ is a straight-chain or branched $C_1$–$C_{20}$-alkyl, $C_3$–$C_8$-cycloalkyl, phenyl, $C_7$–$C_{15}$-arylalkyl, $C_1$–$C_{20}$-alkoxy, oxy, formyl or carboxyl,
$R^2$ and $R^3$ are hydrogen, and
Ar is phenyl, optionally mono- or polysubstituted by a straight-chain or branched $C_1$–$C_6$-alkyl, $C_3$–$C_8$-cycloalkyl, $C_1$–$C_6$-alkoxy, hydroxyl, formyl, oxy, carboxyl, mercapto, amino, halogen or $C_1$–$C_6$-alkylamino.

In a most preferred embodiment, the styrenes are isoeugenol, ferulic acid, coniferyl alcohol, cinnamaldehyde or coniferyl aldehyde.

The process according to the present invention is carried out in the presence of carboxylic acids or carboxylic esters of the formula (II)

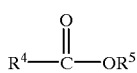
(II)

in which
- $R^4$ is a straight-chain or branched $C_1$–$C_{20}$-alkyl, $C_3$–$C_8$-cycloalkyl, $C_2$–$C_{20}$-alkenyl, $C_5$–$C_8$-cycloalkenyl, $C_2$–$C_{20}$-alkinyl, $C_6$–$C_{14}$-aryl, $C_7$–$C_{15}$-arylalkyl, optionally mono- or polysubstituted by hydroxyl, oxy, formyl, mercapto, $C_1$–$C_6$-alkoxy, $C_1$–$C_6$-alkylamino or halogen, and
- $R^5$ is hydrogen, a straight-chain or branched $C_1$–$C_{20}$-alkyl, $C_3$–$C_8$-cycloalkyl, $C_2$–$C_{20}$-alkenyl, $C_5$–$C_8$-cycloalkenyl, $C_2$–$C_{20}$-alkinyl, $C_6$–$C_{14}$-aryl, $C_7$–$C_{15}$-arylalkyl, optionally mono- or polysubstituted by hydroxyl, oxy, formyl, mercapto, $C_1$–$C_6$-alkoxy, $C_1$–$C_6$-alkylamino or halogen.

Preference is given to using carboxylic acids or carboxylic esters of the formula (II) in which
- $R^4$ is a straight-chain or branched $C_1$–$C_{10}$-alkyl, $C_2$–$C_{10}$-alkenyl, $C_2$–$C_{10}$-alkinyl, $C_3$–$C_8$-cycloalkyl, $C_1$–$C_6$-aryl or $C_7$–$C_{6\,15}$-arylalkyl, and
- $R^5$ is hydrogen, straight-chain or branched $C_1$–$C_{10}$-alkyl, $C_2$–$C_{10}$-alkenyl, $C_2$–$C_{10}$-alkinyl, $C_3$–$C_8$-cycloalkyl, $C_1$–$C_6$-aryl or $C_7$–$C_{15}$-arylalkyl.

The carboxylic acids or carboxylic esters used are most preferably acetic acid or ethyl acetate.

Lipases from *Candida antarctica* are customarily used for the process according to the present invention. Preference is given to lipases from the *Candida antarctica* strains which were deposited at the Deutsche Sammlung von Mikroorganismen [German Depository for Microorganisms] in accordance with the Budapest treaty on the deposition of microorganisms under the following number: DSM 3855, deposited on Sep. 29, 1986, DSM 3908 and DSM 3909, deposited on Dec. 8, 1986.

The lipases are obtainable by a process described in WO 88/02775 from the respective microorganisms:

After the corresponding strain has been cultivated in a suitable nutrient medium under aerobic conditions, liquid enzyme concentrates can be obtained, following removal of insoluble material (e.g., by filtration or centrifugation), by evaporation or reverse osmosis. Solid enzyme preparations can be obtained by precipitation from the soluble concentrate by adding salts or ethanol.

It is known that lipases can also be obtained by recombinant DNA techniques (EP 238 023). In this process, the gene which codes for the lipase is transferred from a selected strain to a recipient organism by methods known to the person skilled in the art. This recipient organism produces the lipase.

In a particularly preferred embodiment, recombinant lipases which have been immobilized on a support material are used. Suitable support materials are, for example, polymers, such as polypropylene, polystyrene, polyvinyl chloride, polyurethane, polyacrylic, latex, nylon or Teflon, polysaccharides, such as agarose or dextran, ion exchanger resins (both cationic and anionic), silicone polymers, such as, for example, siloxanes or silicates, for example, glass. Immobilization techniques for enzymes are known to the person skilled in the art (K. Mosbach, "Immobilized Enzymes", Methods in Enzymology 44, Academic Press, New York, 1976) and include cross-linking, adsorption or covalent bonding to the support material.

Lipases from *Candida antarctica* are also marketed commercially, for example Chirazyme L-2, c-f, lyo (retailer: Roche Diagnostics GmbH, No. 1663917103), Chirazyme L-2, c-f, C2 Lyo (retailer: Roche Diagnostics GmbH, No. 1816969103) or Novozym 435 (Novo Nordisk).

The concentration of hydrogen peroxide required for the process according to the present invention is in the range from 0.05% by volume to 10% by volume. The process according to the present invention is preferably carried out at a hydrogen peroxide concentration of from 0.05% by volume to 5% by volume, particularly preferably at a hydrogen peroxide concentration of from 0.05% by volume to 0.5% by volume.

In order to set the hydrogen peroxide concentration required for the process according to the present invention in the reaction mixture, it is possible to use aqueous hydrogen peroxide solution. Preference is given to using from 30% to 60% (w/v) aqueous hydrogen peroxide solution for adjusting the hydrogen peroxide concentration required in the process according to the present invention.

The hydrogen peroxide solution can be added at the start of the reaction or dropwise during the progress of the reaction.

The hydrogen peroxide concentration in the reaction mixture can also be adjusted by hydrogen peroxide donors which form hydrogen peroxide in situ. Hydrogen peroxide donors are, for example, percarbonates or perborates or the enzyme glucose oxidase in conjunction with glucose.

Preference is given to using the enzyme glucose oxidase in conjunction with glucose as a hydrogen peroxide donor in the process according to the present invention.

The glucose oxidase is preferably from *Aspergillus niger*, which can be used in the process according to the present invention in its native form or in immobilized form. In a preferred embodiment of the process according to the present invention, the glucose oxidase is used in immobilized form.

Customarily, the solvents used for the process according to the present invention are water, aqueous buffers and organic solvents. The organic solvents are, preferably, hexane, cyclohexane, heptane, cycloheptane, toluene, dichloromethane, acetonitrile, dimethylformamide, dioxane, tetrahydrofuran or ethanol. As aqueous buffers, preference is given to using phosphate or acetate buffers.

In a preferred variant of the process according to the present invention, either the styrenes to be oxidized or the carboxylic acids or carboxylic esters are used in excess as solvent. If the carboxylic acids or carboxylic esters are used in the process according to the present invention as solvent, then preference is given to using acetic acid or ethyl acetate.

The process according to the present invention can be carried out with either an excess, or with equimolar amounts or also with a deficit of carboxylic acid or carboxylic ester, based on the styrene used. If the carboxylic acid or the carboxylic ester is used as solvent, then these compounds are in excess, based on the styrene used. If the reaction is carried out in a different solvent, then the carboxylic acid or the carboxylic ester can be used either in an equimolar amount, based on the styrene to be oxidized, or else, in deficit, since these compounds, which are oxidized during the progress of the reaction to give peroxycarboxylic acids as intermediates, are regenerated again to give the corresponding carboxylic acids.

The temperature at which the process according to the present invention is carried out is normally in a range from 1° C. to 95° C., preferably between 10° C. and 70° C., most preferably between 15° C. and 50° C.

The invention is further illustrated but is not intended to be limited by the following examples in which all parts and percentages are by weight unless otherwise specified.

EXAMPLES

Example 1

50 ml of ethyl acetate, 0.82 g (5 mmol) of isoeugenol, 8 ml of 30% (w/v) aqueous hydrogen peroxide solution and 50 mg (122 U) of the lipase Chirazyme L-2, c-f, C2 lyo (Roche Diagnostics GmbH) were mixed in an Erlenmeyer flask. The mixture was shaken at 25° C. for 24 hours on an automatic shaker. To determine the proportion of the desired reaction product vanillin in the mixture, samples were taken from the supernatant after 24 h (analysis data Table 1, line 1). Work-up involved adding potassium permanganate, which removed excess hydrogen peroxide, and drying the samples over sodium sulphate (analysis data Table 1, line 2). The samples were analyzed by gas chromatography using an OV-351 column. The results of the analyses are shown in Table 1, the percentages being calculated from the peak areas in the gas chromatogram. The amount of acetic acid was not included in the calculation.

TABLE 1

| Reaction time | Isoeugenol [GC %] | Vanillin [GC %] |
| --- | --- | --- |
| 24 h | 0.7 | 45.7 |
| 24 h, after work-up | 0.7 | 30.4 |

Example 2

50 ml of ethyl acetate, 3.56 g (20 mmol) of coniferyl aldehyde, 10 ml of 30% (w/v) aqueous hydrogen peroxide solution and 2.5 g (6125 U) of the lipase Chirazyme L-2, c-f, C2 lyo (Roche Diagnostics GmbH) were mixed in an Erlenmeyer flask. The mixture was shaken at 25° C. for 48 hours on an automatic shaker. To determine the content of the desired reaction product vanillin in the mixture, samples were taken from the supernatant after 24 hours and 48 hours, filtered through a sterile filter and dried over sodium sulphate. For work-up, the mixture was treated for 48 hours with potassium permanganate and the resulting manganese dioxide was filtered off. The acetic acid was then neutralized with sodium carbonate, and the solution was washed with ice-water. The organic phase was dried over sodium sulphate and concentrated on a rotary evaporator. The analytical data for the samples after 24 hours and 48 hours and that for the worked-up sample are given in Table 2. The samples were analyzed by gas chromatography using an OV-351 column, the percentages being calculated from the peak areas in the gas chromatogram. The amount of acetic acid was not included in the calculation.

TABLE 2

| Reaction time | Vanillin [GC %] |
| --- | --- |
| 24 h | 82.2 |
| 48 h | 83.7 |
| 48 h, after work-up | 83.1 |

Example 3

50 ml of ethyl acetate, 0.6 g (4.5 mmol) of cinnamaldehyde, 10 ml of 30% (w/v) aqueous hydrogen peroxide solution and 150 mg (360 U) of the lipase Chirazyme L-2, c-f, C2 lyo (Roche Diagnostics GmbH) were mixed in an Erlenmeyer flask. The mixture was shaken at 25° C. for 24 hours on an automatic shaker. To determine the content of the desired reaction products benzaldehyde and phenylacetaldehyde in the mixture, samples were taken from the supernatant, filtered over a sterile filter and dried over sodium sulphate. The samples were analyzed by gas chromatography using an OV-351 column, the percentages being calculated from the peak areas in the gas chromatogram. As a comparison, the reaction was carried out as above, but without the addition of lipase. The results of both experiments are given in Table 3, the amount of acetic acid not being included in the calculation.

TABLE 3

| | Benzaldehyde | Phenyl-acet-aldehyde | Benzoic acid | Cinnamic acid | Cinnam-aldehyde |
| --- | --- | --- | --- | --- | --- |
| with enzyme | 29.1% | 6.2% | 15.9% | 19.4% | 13.0% |
| without enzyme | 0% | 0% | 0.3% | 0.6% | 94.8% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of aromatic carbonyl compounds comprising the step of oxidatively cleaving styrenes in the presence of carboxylic acids or carboxylic esters by lipases and hydrogen peroxide or a hydrogen peroxide donor.

2. A process according to claim 1, wherein styrenes of the formula (I) are used,

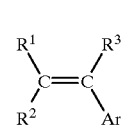

(I)

in which

R$^1$, R$^2$ and R$^3$ independently of one another are hydrogen, straight-chain or branched C$_1$–C$_{20}$-alkyl, C$_3$–C$_8$-cycloalkyl, C$_6$–C$_{14}$-aryl, C$_7$–C$_{15}$-aryl-alkyl, C$_1$–C$_{20}$-alkoxy, C$_1$–C$_{20}$-alkylamino, where the abovementioned hydrocarbon radicals may be mono- or polysubstituted by hydroxyl, formyl, oxy, C$_1$–C$_6$-alkoxy, carboxyl, mercapto, sulpho, amino, C$_1$–C$_6$-alkylamino or nitro or halogen, and Ar is phenyl, optionally mono- or polysubstituted with straight-chain or branched C$_1$–C$_6$-alkyl, C$_3$–C$_8$-cycloalkyl, C$_1$–C$_6$-alkoxy, hydroxyl, oxy, carboxyl, mercapto, sulpho, amino, C$_1$–C$_6$-alkylamino, nitro or halogen.

3. A process according to claim 2, wherein

R$^1$ is a straight-chain or branched C$_1$–C$_{20}$-alkyl, C$_3$–C$_8$-cycloalkyl, phenyl, C$_7$–C$_{15}$-arylalkyl, C$_1$–C$_{20}$-alkoxy, oxy, formyl or carboxyl, R$^2$ and R$^3$ are hydrogen, and Ar is phenyl, optionally mono- or polysubstituted by a straight-chain or branched C$_1$–C$_6$-alkyl, C$_3$–C$_8$- cycloalkyl, $C_1$–$C_6$-alkoxy, hydroxyl, formyl, oxy, carboxyl, mercapto, amino, halogen or $C_1$–$C_6$-alkylamino.

4. A process according to claim 3, wherein said styrenes are selected from the group consisting of isoeugenol, ferulic acid, coniferyl aldehyde or cinnamaldehyde.

5. A process according to claim 1, wherein carboxylic acids or carboxylic esters of the formula (II) are used,

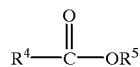

(II)

in which $R^4$ is a straight-chain or branched $C_1$–$C_{20}$-alkyl, $C_3$–$C_8$-cycloalkyl, $C_2$–$C_{20}$-alkenyl, $C_5$–$C_8$-cycloalkenyl, $C_2$–$C_{20}$-alkinyl, $C_6$–$C_{14}$-aryl, $C_7$–$C_{15}$-arylalkyl, optionally mono- or polysubstituted by hydroxyl, oxy, formyl, mercapto, $C_1$–$C_6$-alkoxy, $C_1$–$C_6$-alkylamino or halogen, and $R^5$ is hydrogen, a straight-chain or branched $C_1$–$C_{20}$-alkyl, $C_3$–$C_8$-cycloalkyl, $C_2$–$C_{20}$-alkenyl, $C_5$–$C_8$-cycloalkenyl, $C_2$–$C_{20}$-alkinyl, $C_6$–$C_{14}$-aryl, $C_7$–$C_{15}$-arylalkyl, optionally mono- or polysubstituted by hydroxyl, oxy, formyl, mercapto, $C_1$–$C_6$-alkoxy, $C_1$–$C_6$-alkylamino or halogen.

6. A process according to claim 1, wherein said lipase originates from *Candida antarctica*.

7. A process according to claim 1, wherein said hydrogen peroxide concentration in the reaction mixture is between 0.05% by volume and 10% by volume.

8. A process according to claim 7, wherein said hydrogen peroxide concentration in the reaction mixture is between 0.05% by volume and 5% by volume.

9. A process according to claim 8, wherein said hydrogen peroxide concentration in the reaction mixture is between 0.05% by volume and 0.5% by volume.

10. A process according to claim 1, wherein the hydrogen peroxide concentration in the reaction mixture is formed in situ by the hydrogen peroxide donor glucose oxidase in combination with glucose.

11. A process according to claim 1, wherein said glucose oxidase originates from *Aspergillus niger*.

12. A process according to claim 1, further comprising a solvent which comprises an excess of styrene or carboxylic acid or carboxylic ester.

13. A process according to claim 1, wherein the step of oxidatively cleaving styrenes in the presence of carboxylic acids or carboxylic esters by lipases and hydrogen peroxide or a hydrogen peroxide donor is carried out in a temperature range from 1° C. to 95° C.

* * * * *